United States Patent
Jeon et al.

(10) Patent No.: US 9,909,047 B2
(45) Date of Patent: Mar. 6, 2018

(54) METHOD OF PREPARING DRILLING FLUID AND LUBE BASE OIL USING BIOMASS-DERIVED FATTY ACID

(71) Applicants: SK INNOVATION CO., LTD., Seoul (KR); SK LUBRICANTS CO., LTD., Seoul (KR)

(72) Inventors: Hee Jung Jeon, Daejeon (KR); Wan Seop Kwon, Daejeon (KR); Jin Hee Ok, Busan (KR); Yeon Ho Kim, Daejeon (KR); Yong Woo Kim, Daejeon (KR); Yong Woon Kim, Daejeon (KR)

(73) Assignees: SK INNOVATION CO., LTD., Seoul (KR); SK LUBRICANTS CO., LTD., Seoul (KR)

( * ) Notice: Subject to any disclaimer, the term of this patent is extended or adjusted under 35 U.S.C. 154(b) by 13 days.

(21) Appl. No.: 14/728,258

(22) Filed: Jun. 2, 2015

(65) Prior Publication Data

US 2015/0368537 A1   Dec. 24, 2015

(30) Foreign Application Priority Data

Jun. 2, 2014   (KR) ........................ 10-2014-0066991

(51) Int. Cl.
   *C10G 71/00*   (2006.01)
   *C09K 8/035*   (2006.01)
   (Continued)

(52) U.S. Cl.
   CPC ............ *C09K 8/035* (2013.01); *C07C 31/125* (2013.01); *C09K 8/34* (2013.01); *C10G 3/44* (2013.01);
   (Continued)

(58) Field of Classification Search
   CPC ................................ C10G 3/44; C10G 69/126
   See application file for complete search history.

(56) References Cited

U.S. PATENT DOCUMENTS 5,608,122 A * 3/1997 Buchold ............... C07C 29/149
                                                              568/885
7,459,597 B2   12/2008 Koivusalmi et al.
(Continued)

FOREIGN PATENT DOCUMENTS

| CN | 101484552 A | 7/2009 |
| KR | 20110105579 A | 9/2011 |
| WO | 2007144473 A1 | 12/2007 |

OTHER PUBLICATIONS

European Search Report for EP 15 17 0258 dated Jul. 30, 2015 (5 pages).

(Continued)

*Primary Examiner* — In Suk C Bullock
*Assistant Examiner* — Youngsul Jeong
(74) *Attorney, Agent, or Firm* — Abelman, Frayne & Schwab

(57) ABSTRACT

Disclosed is a method of preparing a drilling fluid and lube base oil using biomass-derived fatty acid, including hydrogenating a fatty acid mixture derived from fat of biological origin so as to be converted into a fatty alcohol mixture, which is then dehydrated to give a C16 and C18 linear internal olefin mixture, which is then oligomerized to give olefinic lube base oil, followed by hydrofinishing to remove the olefin, yielding high-quality lube base oil (e.g. Group III or higher lube base oil). The C16 and C18 linear internal olefin mixture, which is a reaction intermediate, can be utilized as a high-quality drilling fluid.

20 Claims, 9 Drawing Sheets

(51) Int. Cl.
*C09K 8/34* (2006.01)
*C07C 31/125* (2006.01)
*C10G 3/00* (2006.01)
*C10G 69/12* (2006.01)
*C10M 101/04* (2006.01)

(52) U.S. Cl.
CPC ......... *C10G 69/126* (2013.01); *C10M 101/04* (2013.01)

(56) References Cited

U.S. PATENT DOCUMENTS

| | | | |
|---|---|---|---|
| 7,795,484 B2* | 9/2010 | Koivusalmi | C07C 1/24 585/324 |
| 7,888,542 B2 | 2/2011 | Koivusalmi et al. | |
| 8,048,290 B2 | 11/2011 | Knuuttila et al. | |
| 2007/0131579 A1 | 6/2007 | Koivusalmi et al. | |
| 2009/0014354 A1* | 1/2009 | Knuuttila | C10G 29/22 208/58 |
| 2012/0115762 A1 | 5/2012 | Wang et al. | |
| 2012/0238788 A1* | 9/2012 | Wright | B01J 37/06 585/16 |

OTHER PUBLICATIONS

Office Action from Chinese Corresponding Application 201510295662.0 dated Jul. 4, 2016 (9 pages).

\* cited by examiner

PFAD Derived, C16, C18 Alcohol Composition

PFAD Derived, C16, C18 LIO Composition

METHOD OF PREPARING DRILLING FLUID AND LUBE BASE OIL USING BIOMASS-DERIVED FATTY ACID

CROSS-REFERENCE TO RELATED APPLICATION

This application claims the benefit of Korean Patent Application No. 10-2014-0066991, filed Jun. 2, 2014, entitled "Method for Preparing Drilling Fluid and Lube Base Oils Using Biomass-derived Fatty Acid", which is hereby incorporated by reference in its entirety into this application.

BACKGROUND OF THE INVENTION

1. Technical Field

The present invention relates to a method of preparing a drilling fluid and lube base oil using biomass-derived fatty acid. More particularly, the present invention relates to a method of preparing high-quality lube base oil, including hydrogenating a fatty acid mixture derived from biomass of biological origin so as to be converted into fatty alcohol, which is then dehydrated to give a linear internal olefin (LIO), which is then oligomerized to give olefinic lube base oil, followed by hydrofinishing to remove the olefin, yielding high-quality lube base oil (e.g. Group III or higher lube base oil). The linear internal olefin, which is produced during such processes, may be utilized as a drilling fluid.

2. Description of the Related Art

Although oil-based energy has facilitated the development of human society, it suffers from problems including finiteness of resources, regional disparities, environmental pollution, etc., and thus thorough research into fully/partially replacing oil resources with biomass is ongoing.

The term "biomass" broadly refers to any material of biological origin, and narrowly refers to materials mainly derived from plant sources such as corn, soybeans, linseed, sugarcane and palm oil, and may extend to all living organisms, or by-products of metabolism, which is part of the carbon cycle.

Research into the production of high-value-added materials from biomass has been extensively and intensively carried out since the 1970s, but industrially applicable independent examples have not yet arisen. This is considered to be due to certain problems with biomass.

First, biomass resources are limited. Although too much emphasis has been placed on oil resources, they are currently present in amounts that are able to satisfy the global demand for energy and chemicals. Compared to oil resources, biomass, on which less emphasis is laid, requires additional production procedures, and is thus produced at a much lower level.

Second, biomass is not price-competitive. Biomass is produced on the premise of consumption, and thus cheap surplus biomass is difficult to find as a feed for replacing oil resources.

Third, there is difficulty in ensuring that a sufficient amount of biomass is available. Whereas oil resources are produced from preexisting oil deposits in specific areas, thus having no problems related to additional resource yield, biomass typically requires a large area under cultivation and thus it is difficult to ensure the production of biomass in sufficient amounts to serve as a resource to replace oil.

Finally, products using biomass are conventionally limited to inexpensive materials such as gasoline or diesel, making it difficult to propose independently commercially available models without political support.

However, techniques for overcoming the above limitations with improvements in biomass production are being devised these days. In particular, crude palm oil (CPO) and soybean oil (SBO), presented as surplus biomass, are globally produced in amounts on the order of millions of tons, and amounts that are able to be ensured on the open market are approximately 1 million tons or more. Furthermore, as the production amount thereof increases, price volatility is reduced, and purchase on the open market becomes possible. Also, crude palm oil is receiving attention as an alternative to oil-based products because the availability of large amounts thereof can be ensured and its price is stable on the open market. Furthermore, crude palm oil is composed of 90~95% triglyceride, and the ratio of C16 and C18 carbon chains of triglyceride approximates 45:55 (by weight). A material corresponding to 5~10 wt %, which is the remainder of crude palm oil other than triglyceride, is composed of C16 and C18 fatty acids, containing about 10% mono- or di-glyceride. Triglyceride, which is selectively separated through refinement of crude palm oil, is referred to as RBD (Refined Bleached Deodorized) palm oil. As such, the fatty acid and mono- or di-glyceride amounting to about 5~10 wt %, which were removed, may be referred to as a palm fatty acid distillate (PFAD).

Currently, the amounts of crude palm oil and palm fatty acid distillate that can be purchased on the open market are about 1 million tons and about 4 hundred thousand tons, respectively. In this regard, the fatty acids that constitute triglyceride and palm fatty acid distillate are illustrated in FIG. 1. Also, the compositions of the carbon branches for crude palm oil (CPO) and palm fatty acid distillate (PFAD) are shown in Table 1 below.

TABLE 1

| Fatty acid | CPO[1] (wt %) | PFAD[2] (wt %) |
|---|---|---|
| 14:0 Myristic | 0.5~5.9 | 0.9~1.5 |
| 16:0 Palmitic | 32~59 | 43~51 |
| 16:1 Palmitoleic | <0.6 | — |
| 18:0 Stearic | 1.5~8.0 | 4~5 |
| 18:1 Oleic | 27~52 | 33~40 |
| 18:2 Linoleic | 5.0~14 | 9~11 |
| 18:3 Linolenic | <1.5 | 0.2~0.6 |
| 20:0 Eicosanoic | <1.0 | — |

[1]composed mainly of triglyceride
[2]composed mainly of fatty acid

Compared to fuels, models for use in the commercial preparation of high-value-added products, such as lube base oil, from biomass have been proposed. For example, the production of Group III lube base oil from a feed containing 50% or more of an unsaturated compound via oligomerization, deoxygenation and isodewaxing (IDW) is known (e.g. U.S. Pat. Nos. 7,459,597 and 7,888,542).

The aforementioned techniques are mainly utilized to polymerize olefins present in biomass. To attain high reaction activity, the amount of olefin in a feed is required to be 50% or more, and naphthene-based lube base oil containing about 72% naphthene is obtained by random polymerization. In particular, isodewaxing is performed to improve the fluidity of lube base oil. Also, techniques for preparing lube base oil from fatty acid via pre-hydrotreatment, ketonization, hydrodeoxygenation (HDO) and isodewaxing are known (e.g. U.S. Pat. No. 8,048,290, etc.). Thereby, the yield of the product (Group III lube base oil) relative to the feed (fatty acid) is mentioned to be about 36%.

In addition, a process of preparing Group V lube base oil corresponding to ester-based lube base oil and 1-decene as the feed for poly alpha olefin (PAO) from triglyceride is known (U.S. Patent Application Publication No. 2012/0115762). This process includes metathesis, oligomerization, and hydroisomerization. As such, in order to ensure economic benefits, it is important to increase the proportion of C18:1, and there is a need to suppress the inactivation of precious metal catalysts and the collapse of ester structures in the hydrogenation for the skeletal isomerization of ester.

SUMMARY OF THE INVENTION

Therefore, an embodiment of the present invention is intended to provide a method of economically efficiently preparing a drilling fluid and high-quality lube base oil (particularly, Group III or higher lube base oil, and more particularly Group III+ lube base oil) through a reaction route that is different from conventional techniques for preparing lube base oil from biomass-derived fatty acid.

The present invention pertains to a method of preparing a drilling fluid and lube base oil using a fatty acid derived from a biomass. In accordance with an embodiment thereof, the method comprises: a) providing a biomass-derived fatty acid mixture; b) hydrogenating the fatty acid mixture to give a fatty alcohol mixture; c) dehydrating the fatty alcohol mixture to give a C16 and C18 linear internal olefin mixture; d) oligomerizing the C16 and C18 linear internal olefin mixture to give olefinic lube base oil; and e) hydrofinishing the olefinic lube base oil, yielding Group III or higher lube base oil.

In an exemplary embodiment, the biomass may be animal biomass, plant biomass, or a combination thereof, the animal biomass may comprise fish oil, cattle oil, lard, sheep oil, or butter, and the plant biomass may comprise sunflower seed oil, canola oil, coconut oil, corn oil, cottonseed oil, rapeseed oil, linseed oil, safflower oil, oat oil, olive oil, palm oil, peanut oil, apricot kernel oil, almond oil, avocado oil, camellia oil, rice bran oil, walnut oil, rape oil, flaxseed oil, sesame oil, soybean oil, castor oil, cocoa butter, or palm kernel oil.

In an exemplary embodiment, the fatty acid mixture may contain at least 80 wt % of C16 fatty acid, C18 fatty acid, or a combination thereof.

In an exemplary embodiment, the fatty acid mixture provided in a) may have 4 to 24 carbon atoms.

In an exemplary embodiment, the fatty acid mixture provided in a) may be a fatty acid mixture produced by de-esterification of a triglyceride in the biomass.

In an exemplary embodiment, the fatty acid mixture may be a palm fatty acid distillate (PFAD) separated from the biomass.

In an exemplary embodiment, b) may be performed in the presence of a metal-carrier catalyst, and the catalyst may be configured such that at least one metal selected from among Groups 8 to 11 metals on the periodic table is loaded on at least one carrier selected from among alumina ($Al_2O_3$), silica ($SiO_2$), silica-alumina, zeolite, mesoporous silica, SAPO, and AlPO.

In an exemplary embodiment, the metal may comprise at least one selected from among copper (Cu), chromium (Cr), zinc (Zn), and aluminum (Al).

In an exemplary embodiment, the hydrogenating in b) may be performed under conditions of a temperature of 150~500° C. and a pressure of 100 bar or less.

In an exemplary embodiment, the hydrogenating in b) may be performed under conditions of a temperature of 250~400° C. and a pressure of 50 bar or less.

In an exemplary embodiment, c) may be performed in the presence of a metal oxide catalyst, and the catalyst may comprise alumina, silica-alumina, kaolin clay, SAPO, AlPO, zirconia, titania, iron oxide, vanadium oxide, zeolite, alumina-loaded mesoporous silica, or mixtures thereof.

In an exemplary embodiment, the dehydrating in c) may be performed by adjusting a reaction temperature and a retention time, so that shift of a position of a double bond in an olefin is controlled, thus controlling the C16 and C18 linear internal olefin mixture.

In an exemplary embodiment, the reaction temperature may be 250~500° C., and a space velocity may be 0.01~50 $hr^{-1}$.

In an exemplary embodiment, the oligomerizing in d) may be performed in the presence of a cation polymerization catalyst.

In an exemplary embodiment, the cation polymerization catalyst may comprise at least one selected from among catalysts configured such that aluminum (Al) is loaded on zeolite, clay, SAPO, AlPO, and mesoporous silica.

In an exemplary embodiment, the oligomerizing in d) may be performed at 120~400° C.

In an exemplary embodiment, the hydrofinishing in e) may be performed using a catalyst configured such that at least one metal selected from among platinum (Pt), palladium (Pd), nickel (Ni), iron (Fe), copper (Cu), chromium (Cr), vanadium (V), and cobalt (Co) is loaded on at least one support selected from among alumina, silica, silica-alumina, zirconia, ceria, titania, zeolite, clay, SAPO, and AlPO.

In an exemplary embodiment, the hydrofinishing in e) may be performed under conditions of a temperature of 150~500° C., an $H_2$ pressure of 5~200 bar, and a gas oil ratio ($H_2$/feed ratio) of 300~2000 $Nm^3/m^3$.

In an exemplary embodiment, the C16 and C18 linear internal olefin mixture in c) may be an olefinic hydrocarbon-based drilling fluid.

In an exemplary embodiment, the drilling fluid may be a linear or branched hydrocarbon having a pour point of −9° C. or less and containing an olefin, without aromatics.

In an exemplary embodiment, the lube base oil may be branched paraffin having 32 or more carbon atoms.

In an exemplary embodiment, the lube base oil may have a viscosity index of at least 137, a pour point of −24° C. or less, and a cloud point of −20° C. or less.

According to embodiments of the present invention, industrially applicable drilling fluids or high-quality lube base oil can be prepared from biomass-derived C16 and C18 fatty acid mixtures.

Also, the position of the double bond of an olefin derived from biomass alone can be adjusted, thus controlling the properties of the drilling fluid or lube base oil.

In particular, as the reaction conditions for dehydration are modulated, important product characteristics, including the pour point of drilling fluid, or the viscosity index, pour point, etc. of lube base oil, can be controlled, even without the use of an additional reaction for adjusting the properties.

Since the quality of lube base oil can be controlled depending on the need even by the use of any fatty acid derived from biomass, wide applications thereof are expected by virtue of high economic impact, so long as the economical supply of such a feed is ensured.

DESCRIPTION OF SPECIFIC EMBODIMENTS

The present invention may be embodied by the following description with reference to the appended drawings. The following description is provided to facilitate an understanding of specific embodiments of the present invention, and the present invention is not necessarily limited thereto.

The present invention addresses a method of preparing a drilling fluid and lube base oil from biomass-derived fatty acid.

In an embodiment of the present invention, the above method includes providing a biomass-derived fatty acid mixture, hydrogenating the fatty acid mixture to give a fatty alcohol mixture, dehydrating the fatty alcohol mixture to give a C16 and C18 linear internal olefin (LIO) mixture, oligomerizing the C16 and C18 linear internal olefin mixture to give olefinic lube base oil, and hydrofinishing the olefinic lube base oil, yielding Group III or higher lube base oil.

Figure 1:
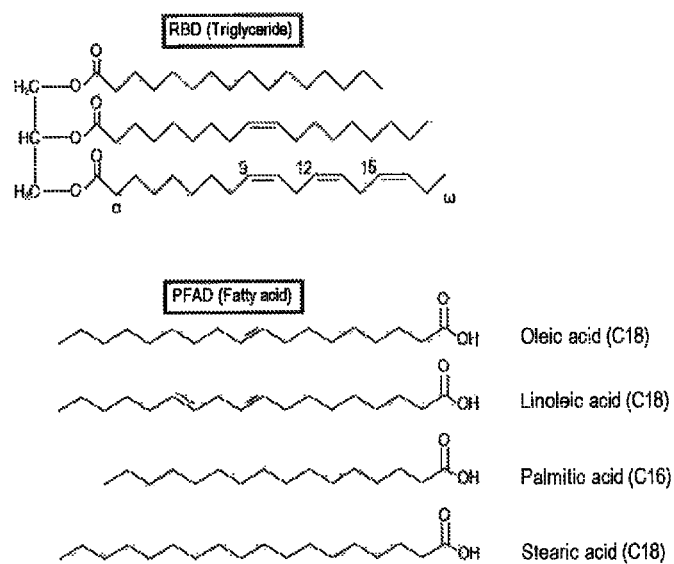
FIG. 1 illustrates chemical formulas of triglyceride and fatty acid contained in typical crude palm oil.
Figure 2:
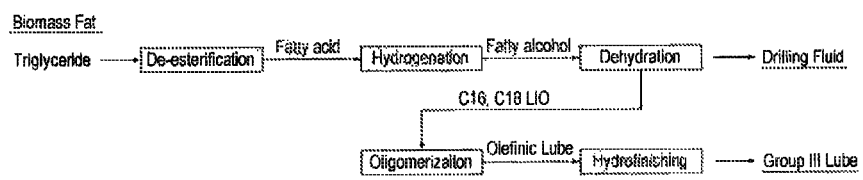
FIG. 2 schematically illustrates a process of preparing a drilling fluid and lube base oil from biomass-derived fatty acid according to an exemplary embodiment of the present invention.

In an embodiment of the present invention, as illustrated in FIG. 2, the biomass-derived fatty acid is sequentially subjected to hydrogenation and dehydration, thus producing a C16 and C18 linear internal olefin mixture, which may be utilized as a drilling fluid.

As used therein, the term "C16 and C18 linear internal olefin mixture" refers to a linear hydrocarbon composed of 16 or 18 carbon atoms, and may be defined as a mixture of olefins containing unsaturated double bonds at the middle portion of the molecule, but not the terminal portion thereof.

Table 2 below shows the criteria of the properties of a hydrocarbon usable as a drilling fluid.

TABLE 2

| Properties | Range |
| --- | --- |
| Flash point | About 85° C. or more |
| Pour point | Less than about −5° C. |
| Density (g/cm$^3$) | About 0.77~0.81 |
| Kinematic viscosity (cst: 40° C.) | About 1.9~3.5 |
| Aromatics (wt %) | About 5 wt % or less (particularly 2 wt % or less, and more particularly substantially none) |
| Others (S, N, transition metal and/or halogen) (wt %) | About 1 wt % or less (particularly about 0.5 wt % or less, and more particularly substantially none) |

Drilling fluids have to satisfy specific properties, taking into consideration the fundamental functions required thereof. For example, the density is related with the function that allows a fluid column to exhibit characteristics similar to lithostatic stress in ice depending on changes in the drilling depth. Also, when the pour point of the drilling fluid is high, the viscosity of the drilling fluid may drastically increase in a low-temperature environment (including deep-water drilling, oil drilling in polar regions, etc.), and also excessive thickening may occur.

Furthermore, a low flash point may cause stability problems. In addition, excessively low viscosity makes it impossible to exhibit the inherent function of a drilling fluid for transferring cuttings to the surface thereof through floating, whereas excessively high viscosity makes it difficult to pump the drilling fluid. Hence, the viscosity has to be set within a suitable range. However, there is a tradeoff between these properties (i.e. when either property is improved, the other property suffers), making it difficult to simultaneously impart the properties required of the drilling fluid alone.

Recently, as regulations for environmental pollution and the work environment resulting from drilling have become more stringent, drilling fluid is required not only to manifest its inherent functions but also to avoid causing human health or environmental problems. However, for conventional techniques, limitations are imposed on minimizing negative effects on the environment, such as biodegradability and/or toxicity. For example, an oil-based drilling fluid essentially contains impurities present in crude oil, such as polycyclic aromatics, transitional metals, sulfur, nitrogen, and halogen, and thus additional systems or processes for removing such impurities must be provided.

Also, a synthetic drilling fluid, especially a product obtained by oligomerization of an olefin, has potential drawbacks because the catalyst (e.g. boron trifluoride, etc.) used for reaction may be discharged in the form of a toxic material. Moreover, biodegradability, sediment toxicity, heavy metals, and polycyclic aromatic content are more strictly regulated by the Environmental Protection Agency (EPA) in the USA.

In the embodiment of the present invention illustrated in FIG. 2, the biomass-derived fatty acid is subjected to hydrogenation, dehydration, oligomerization, and hydrofinishing, yielding high-quality lube base oil.

Examples of lube base oil are classified depending on the mechanical and chemical properties thereof, based on API, as shown in Table 3 below.

TABLE 3

| | Viscosity index | Sulfur (wt %) | Pour point (° C.) | Saturated (wt %) |
|---|---|---|---|---|
| Group I | 80 to 119 | >0.03 | −5 to 15 | <90 |
| Group II | 80 to 119 | ≤0.03 | −10 to −20 | ≥90 |
| Group III | ≥120 | ≤0.03 | −10 to −25 | ≥90 |
| Group III+ | ≥140 | ≤0.03 | −15 to 30 | >90 |
| Group IV | 135 to 140 | — | −53 | — |
| Group V | 140 | — | −21 | — |

To manufacture lube base oil from biomass-derived fat (triglyceride and/or fatty acid), conventional processes include oligomerization of olefins already present in biomass, ketonization of fatty acids, and decomposition of triglyceride. In particular, the oligomerization of olefin already present in biomass requires an additional isomerization process to decrease the pour point thereof; and the preparation activity of lube base oil is determined depending on the olefin content of the feed. Also, the ketonization of fatty acid requires isomerization because the carbon chain of fatty acid is too long. Furthermore, the decomposition of triglyceride may be significantly affected by the number of carbon atoms in triglyceride branches and the number of double bonds thereof.

With regard thereto, hydrogenation, dehydration, oligomerization and hydrofinishing are sequentially carried out in the embodiment of the present invention. Instead of oligomerization by double bonds randomly present in the structure of biomass-derived fatty acid as in conventional techniques, in the present embodiment, the position of the double bond in an olefin produced by dehydrating fatty alcohol derived from fatty acid is controlled, yielding a drilling fluid having various properties. Furthermore, selective oligomerization thereof is performed, thus obtaining lube base oil having a structure similar to the radially symmetrical structure of PAO (Poly Alpha Olefin). Thereby, high-quality lube base oil (e.g. Group III or higher lube base oil, especially Group III+ lube base oil) having a high viscosity index, a low pour point, and a low cloud point can result, even without the use of isomerization. By means of the above processes, regardless of which specific biomass-derived fatty acid is used as the feed, a drilling fluid and lube base oil having various properties may be reproducibly manufactured.

Specifically, as the position of the double bond in the olefin mixture (especially the C16 and C18 olefin mixture) converted from the biomass-derived fatty acid mixture is close to the alpha position, the pour point of the resulting drilling fluid may increase, and not only the viscosity index of the lube base oil but also the pour point and cloud point thereof may increase. In contrast, as the position of the double bond is close to the center of the hydrocarbon chain, the pour point of the resulting drilling fluid may decrease and the viscosity index, pour point and cloud point of lube base oil may decrease. With the goal of tuning the properties of the drilling fluid and the final lube base oil, the dehydration conditions of the fatty alcohol, even by the use of fatty acid feed, may be changed, so that the position of the double bond in the olefin mixture may be shifted. As in the embodiment of the present invention, oligomerization mainly occurs at the alpha double bond (or shifted double bond) in the olefin produced by the dehydration of fatty alcohol, and the resulting oligomer has a radially symmetrical structure and may thus possess a low pour point and a low cloud point despite the large number of carbon atoms (e.g. about 30 or more).

Providing Biomass-Derived Fatty Acid

According to an embodiment of the present invention, biomass may be obtained using various animal and plant fat components known in the art. The animal components may be exemplified by fish oil, cattle oil, lard, sheep oil, butter, etc., and examples of the plant components may include sunflower seed oil, canola oil, coconut oil, corn oil, cottonseed oil, rapeseed oil, linseed oil, safflower oil, oat oil, olive oil, palm oil, peanut oil, apricot kernel oil, almond oil, avocado oil, camellia oil, rice bran oil, walnut oil, rape oil, flaxseed oil, sesame oil, soybean oil, castor oil, cocoa butter, or palm kernel oil. These components may be used alone or in combination. Also, the fatty acid of the present invention is not limited to the species listed above. The kind of biomass usable in the present embodiment, the fatty acids contained therein and the amounts thereof are given in Tables 4 and 5 below.

TABLE 4

| Fatty acid | Soybean oil | Corn oil | Cottonseed oil | Sunflower seed oil | Peanut oil | Olive oil | Rape oil |
|---|---|---|---|---|---|---|---|
| 14:0 Myristic | 0.4 | <0.1 | 0.4-2.0 | <0.5 | <0.4 | 0.05 | <1.0 |
| 16:0 Palmitic | 7~14 | 8~9 | 17~31 | 3~10 | 6.0~16 | 7.5~20 | 1.5~6.4 |
| 16:1 Palmiloleic | <0.5 | <0.5 | 0.5~2.0 | <1.0 | <1.0 | 0.3~3.5 | <3.0 |
| 18:0 Stearic | 1.4~5.5 | 0.5~4.0 | 1.0~4.0 | 1.0~10 | 1.3~6.5 | 0.5~3.5 | 0.5~3.1 |
| 18:1 Oleic | 19~30 | 19~50 | 13~44 | 14~65 | 35~72 | 56~83 | 8~45 |
| 18:2 Linoleic | 44~62 | 34~62 | 33~59 | 20~75 | 13~45 | 3.5~20 | 11~29 |
| 18:3 Linolenic | 4.0~11 | <2.0 | 0.1~2.1 | <0.7 | <1.0 | <1.5 | 5~16 |
| 20:0 Eicosanoic | <1.0 | <1.0 | <0.7 | <1.5 | 1.0~3.0 | | <3.0 |
| 20:1 Eicosenoic | <1.0 | | <0.5 | <0.5 | 0.5~2.1 | | 3~15 |
| 22:0 Docosanoic | | <0.5 | <0.5 | <1.0 | 1.0~5.0 | | <2.0 |
| 22:1 Erucic | | | | <0.5 | <0.5 | <2.0 | 5~60 |
| 24:0 Tetracosanoic | | <0.5 | <0.5 | <0.5 | 0.5~3.0 | | <2.0 |
| 24:1 Tetracosenoic | | | | <0.5 | | | |

TABLE 5

| Fatty acid | Cocoa butter | Palm oil | Palm kernel oil | Coconut oil | Butter | Lard | Cattle oil |
|---|---|---|---|---|---|---|---|
| 4:0 Butyric | | | | | 3.6 | | |
| 6:0 Caproic | | | <0.5 | <1.2 | 2.2 | | |
| 8:0 Caprylic | | | 2.4~62 | 3.4~15 | 1.2 | | |
| 10:0 Capric | | | 2.6~7.0 | 3.2~15 | 2.8 | | |
| 12:0 Lauric | | <1.2 | 41~55 | 41~56 | 2.8 | | |
| 14:0 Myristic | 0.1 | 0.5~5.9 | 14~20 | 13~23 | 10.1 | 2.0 | 2.5 |
| 14:1 Myristoleic | | | | | | | 3.0 |
| 16:0 Palmitic | 26.0 | 32~59 | 6.5~11 | 4.2~12 | 25.0 | 27.1 | 27.0 |
| 16:1 Palmitoeic | 0.3 | <0.6 | 1.3~3.5 | 1.0~4.7 | 2.6 | 4.0 | 10.8 |
| 18:0 Stearic | 34.4 | 1.5~8.0 | 10~23 | 3.4~12 | 12.1 | 11.0 | 7.4 |
| 18:1 Oleic | 34.8 | 27~52 | 0.7~54 | 0.9~3.7 | 27.1 | 44.4 | 47.5 |
| 18:2 Linoleic | 3.0 | 5.0~14 | | | 2.4 | 11.4 | 1.7 |
| 18:3 Linolenic | 0.2 | <1.5 | | | 2.1 | | 1.1 |
| 20:0 Eicosanoic | 1.0 | <1.0 | | | | | |
| 22:0 Docosanoic | 0.2 | | | | | | |

As is apparent from Tables 4 and 5, the number of carbon atoms of the fatty acids contained in biomass derived from various animal and plant components falls in the range of about 4~24, and especially, C16 and C18 fatty acids are most prevalent. Illustratively, the amount of C16 fatty acid, C18 fatty acid or a combination thereof in the fatty acids may be at least about 80 wt %, particularly at least about 85 wt %, and more particularly about 90~99 wt %. Also, fatty acids having various numbers of carbon atoms depending on the origin of biomass may be contained therein.

As mentioned above, the biomass-derived fat component may mainly contain triglyceride and fatty acid. As such, the ratio (by weight) of triglyceride to fatty acid ranges for example from about 100:1 to 6:1, particularly from about 20:1 to 6:1, and more particularly from about 10:1 to 6:1, and may vary depending on the biomass source, and is not necessarily limited to the above numerical ranges.

Also, the carbon chain of triglyceride is approximately composed of C4~C24, and more typically of C16 and C18. Such triglyceride or some of mono- and di-glycerides may be converted into a fatty acid mixture by de-esterification, as represented by Scheme 1 below.

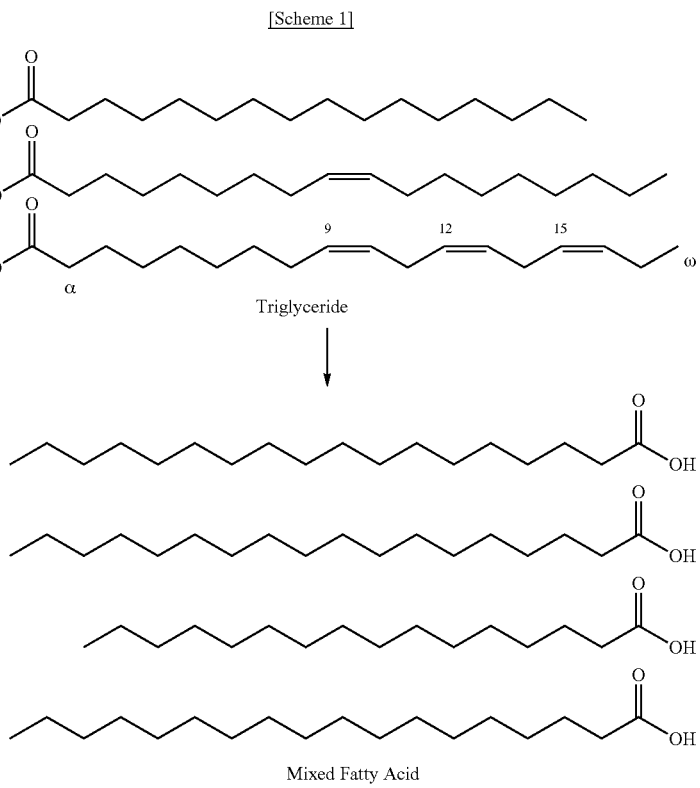

[Scheme 1]

Triglyceride

Mixed Fatty Acid

De-esterification as illustrated in Scheme 1 is a typical reaction for preparing fatty acid methyl ester (FAME) from biomass.

In an exemplary embodiment, de-esterification enables the conversion of a feed into fatty acid using a strong acid (e.g. $H_2SO_4$, $HNO_3$) or a strong base (e.g. NaOH, KOH) in the presence of steam at high temperature (typically about 100~300° C., more typically about 100~200° C.). In addition, various reactions for converting triglyceride into fatty acid as known in the art may be adopted without particular limitation.

As for the preparation of fatty acid as shown in Scheme 1, the selection of a biomass feed is regarded as important. Although any biomass fat may be applied in the present embodiment, crude palm oil and soybean oil may be adopted as the biomass feed by virtue of their industrial availability, production markets, and price stability. Such a biomass feed is produced in an amount of hundreds of tons per year, of which the amount purchasable on the open market is about one hundred tons or more, and thus an industrially applicable amount may be stably ensured.

For the above feed, triglyceride of the fat is composed mainly of C16 and C18 carbon chains. For example, a C16/C18 ratio is about 1 in crude palm oil, and is about 0.25 in soybean oil. In order to apply the above feed to specific uses (e.g. processed food or cosmetic ingredients), triglyceride may be selectively isolated. As such, the material remaining after separation is a palm fatty acid distillate composed mostly of fatty acid (typically comprising about 90% or more of C16 and C18 fatty acids). Accordingly, the material of crude palm oil other than RBD (Refined Bleached Deodorized) palm oil corresponding to triglyceride may be referred to as a palm fatty acid distillate, and the material of soybean oil other than triglyceride may be referred to as a soy fatty acid distillate (SFAD). Such a palm fatty acid distillate is conventionally regarded as a byproduct created in the course of refining triglyceride, and its end use is limited and thus it is traded relatively cheaply.

Therefore, in an embodiment of the present invention, the palm fatty acid distillate separated from biomass, which has superior price competitiveness and can be manufactured at the level of individual plants to prepare lube base oil, may be utilized as a fatty acid mixture.

Hydrogenation (Conversion of Fatty Acid into Fatty Alcohol)

In an embodiment of the present invention, the biomass-derived fatty acid mixture may be converted into a fatty alcohol mixture by hydrogenation using a fixed bed reactor.

In an embodiment of the present invention, the reaction for converting a fatty acid mixture into a fatty alcohol by hydrogenation may be carried out using any kind of catalyst. Particularly useful is a catalyst configured such that at least one metal selected from among Groups 8 to 11 metals on the periodic table, more specifically, at least one metal selected from among copper (Cu), chromium (Cr), zinc (Zn) and aluminum (Al), is loaded on a carrier such as alumina ($Al_2O_3$), silica ($SiO_2$), silica-alumina, zeolite, mesoporous silica, SAPO or AlPO. In an exemplary embodiment, hydrogenation may be carried out using a $CuZnCrO_x$ catalyst, a $CuCr/Al_2O_3$ catalyst, or a $Cu/SiO_2$ catalyst.

The hydrogenation of the fatty acid mixture may be implemented under conditions of a temperature of about 150~500 r (particularly about 200~450° C., and more particularly about 250~400° C.), an $H_2$ pressure of about 100 bar or less (particularly about 50 bar or less, and more particularly about 1~70 bar), a weight hourly space velocity (WHSV) of about 0.05~10 $hr^{-1}$ (particularly about 0.1~3 $hr^{-1}$, and more particularly about 0.5~2 $hr^{-1}$), and a gas oil ratio (GOR) of about 50~5000 (particularly about 300~2500, and more particularly about 500~1500). The above reaction may be carried out in a batch mode or a continuous mode, but is economically efficiently carried out using a fixed-bed reactor for large-scale industrial applications.

The reaction for converting an acid into an alcohol may include two steps. In lieu of the direct conversion of an acid into an alcohol, the acid may be converted into an ester intermediate, which is then converted into an alcohol by hydrogenation. Thus, such a reaction may include the steps of converting the acid into the ester and then converting the ester into the alcohol through partial hydrogenation. Although these two steps take place in sequence, the reaction rate itself is high, and thus the operating conditions where the yield of the ester intermediate is low may be found. For this reason, the reaction for converting the acid into the alcohol may include the use of an additional alcohol to facilitate the conversion into an ester intermediate. Typically, an additional alcohol may be exemplified by a cheap alcohol such as methanol. The acid is introduced with such an additional alcohol, and is then subjected to esterification to produce an ester, which is then converted into the alcohol, which may be briefly described by Scheme 2 below.

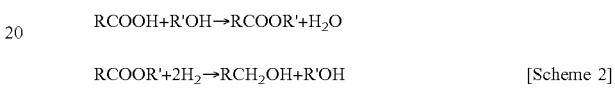

As shown in Scheme 2, since the additional alcohol, which is used to convert the acid into the alcohol, has no structural changes after the reaction, it may be recovered, and may thus be recycled. However, a cheap volatile alcohol such as methanol may not be recovered.

In contrast, the reaction may be induced by the acid alone, without the use of the additional alcohol. As such, the reaction of Scheme 3 below may be carried out.

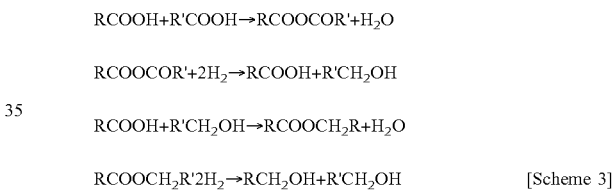

As shown in Scheme 3, even when no additional alcohol is used, the acid may be converted into a condensation polymer (an acid anhydride), further converted into an ester, and then finally converted into an alcohol. The case where no additional alcohol is used is favorable in terms of profitability and reaction efficiency. However, the condensation activity of the acid is not high, and the total reaction efficiency is low compared to when the ester intermediate is directly produced by the addition of the acid. Hence, the above case is not typically adopted. Thus, the reaction for converting the acid into the alcohol in the absence of the additional alcohol is generally employed only in the initial reaction for preparing an alcohol to be introduced together with the acid when low-grade alcohol such as methanol is not directly added. The reaction where the acid alone is converted into the alcohol upon initial operation and the alcohol thus made is introduced again is typically applied. Although the production cost is low when inducing an alcohol conversion reaction using the acid alone, compared to when using the cheap light alcohol, the use of light alcohol is desirable taking into consideration the reaction yield or the operating conditions, and is thus mainly adopted.

Dehydration (Conversion of Fatty Alcohol into C16 and C18 Linear Internal Olefin Mixture)

In an embodiment of the present invention, the biomass-derived fatty acid mixture may be converted into a fatty alcohol mixture by hydrogenation. The fatty alcohol converted by hydrogenation may be subjected to dehydration using a metal oxide catalyst in a fixed-bed reactor, and may thus be converted into a C16 and C18 linear internal olefin mixture.

Also, the C16 and C18 linear internal olefin mixture may be an olefinic hydrocarbon-based drilling fluid.

Upon dehydration, the extent of shifting of the position of the double bond in the olefin may be adjusted using the reaction temperature and the retention time, thus controlling the C16 and C18 linear internal olefin mixture.

In an embodiment, the metal oxide catalyst used to dehydrate the fatty alcohol so as to be converted into an olefin may be used without limitation so long as it has a weak acid site. For example, a material having a weak acid site, such as zirconia, is treated under the condition that the reaction temperature is increased, whereas a material having a strong acid site, such as zeolite, is treated under the condition that the reaction temperature is decreased, thereby enabling control of the shift in position of the double bond in the olefin.

The metal oxide usable as the catalyst is typically exemplified by alumina, silica-alumina, kaolin clay, SAPO, AlPO, zirconia, titania, iron oxide, vanadium oxide, zeolite, alumina-loaded mesoporous silica, or mixtures thereof. The present invention is not limited to the above metal oxides.

The dehydration may be carried out at 250~500° C. When the reaction conditions are controlled, efficient olefin conversion through dehydration of fatty alcohol may occur at 250° C. As the reaction temperature is gradually increased, not only the olefin conversion but also the double bond position shift reaction may take place, thus gradually increasing the proportion of centered olefin. Also, in the case where the reaction pressure is increased, activation energy necessary for the actual reaction is sufficient, but the feed may be converted into a phase that makes it difficult to participate in the reaction, so that the position shift reaction of the double bond of the olefin may occur to a lesser extent. Also, in the case where the space velocity (WHSV) is increased, the amount of the feed to be processed relative to the amount of the unit catalyst is increased, and the position shift reaction of the unsaturated double bond occurs to a lesser extent. Also, in the case where the gas oil ratio (GOR) is increased, the retention time when the feed is present on the surface of the catalyst is shortened, thus decreasing the position shift reaction of the unsaturated double bond.

Depending on the extent of dehydration, it is possible to shift the position of the double bond in the olefin during the reaction. The olefin produced by controlling the above reaction conditions may be a linear internal olefin, but not the linear alpha olefin. For the linear internal olefin, the position distribution of the double bond in the olefin may be controlled.

The reactor may be specifically exemplified by a fixed-bed reactor, and the reaction conditions of the fixed-bed reactor include a nitrogen ($N_2$) flow rate of 10~1000 sccm, and specifically 30~200 sccm. A cheaper inert carrier gas, but not the nitrogen ($N_2$), may be applied. Furthermore, argon (Ar), helium (He), etc. may be applied, in place of nitrogen. The space velocity (WHSV) may be set to 0.01~50 $hr^{-1}$, and particularly 0.1~3 $hr^{-1}$.

After the dehydration, all or some of the linear internal olefins obtained by separation may be recycled. Furthermore, in consideration of such recycling, the amount of centered olefin can be drastically increased. When only the operating conditions are controlled during the dehydration, the centered olefin, in which the double bond in the olefin is positioned at the center, may be mostly prepared. However, when a catalyst having very high or low activity is used, the linear internal olefin may be recycled in consideration of operating stability.

Also, as the position of the double bond in the olefin moves toward the center of the linear hydrocarbon, the distance between molecules increases, and the pour point and the cloud point may be advantageously expected to decrease. Thereby, a high-quality drilling fluid and Group III or higher lube base oil through oligomerization thereof may be manufactured.

Oligomerization

According to an embodiment of the present invention, the C16 and C18 linear internal olefin mixture produced by dehydration may be oligomerized. Specifically, oligomerization of the olefin converted by dehydration may result in olefinic lube base oil having a double bond.

As such, typical examples of the oligomer may include dimers and/or trimers, and may further include a small amount of tetramers or larger oligomers. If an olefin produced by dehydration has a smaller number of carbon atoms other than C16 and C18, trimers or larger oligomers may be mainly contained. In particular, an olefin having 10 or less carbon atoms may be composed mainly of tetramers or larger oligomers. On the other hand, if the number of carbon atoms of the olefin is 16 or more, dimers may be contained as the main component.

Furthermore, the oligomerization is carried out at the double bond formed by dehydration, but may additionally take place at the double bond already present in the biomass-derived fatty acid. In the course of hydrogenation, most of the olefins in the biomass may be saturated and removed, but some of them may be left behind, and may thus have an influence on the radial symmetry of the oligomer and thereby on the viscosity index. Hence, the reaction conditions for partial hydrogenation and dehydration have to be properly controlled.

In an embodiment of the present invention, the catalyst for use in oligomerization may include a cation polymerization catalyst, a metallocene catalyst, and a Ziegler-Natty catalyst. Typically useful is a cation polymerization catalyst.

In an exemplary embodiment, the cation polymerization catalyst may include at least one selected from among zeolite, and clay (particularly montmorillonite and kaolin), and furthermore, a cation polymerization catalyst having a structure of SAPO or AlPO may be used. Alternatively, a catalyst configured such that aluminum (Al) is loaded on mesoporous silica such as SBA-15, MCM-41 or MCM-48 (the amount of Al is about 0.1~50 wt %, and particularly about 5~35 wt %) may be used.

The zeolite may include at least one of Y-zeolite (especially USY zeolite having high a silica alumina ratio (SAR)), ZSM-5, and beta-zeolite. Particularly useful as Y-zeolite is USY zeolite having an SAR of about 0.5 or more, particularly about 12 or more, more particularly about 30~150, and still more particularly about 50~100.

In addition thereto, a metal catalyst having a hydrotalcite or spinel structure or a strong-acid-site catalyst such as niobic acid may be used. Furthermore, useful is an RFCC catalyst including Y-zeolite and kaolin (e.g. the mixing ratio of Y zeolite and kaolin is about 5 to 50 wt %), and particularly useful is an RFCC flash catalyst or an RFCC equilibrium catalyst (E-cat.).

In an exemplary embodiment, the oligomerization reaction in the presence of the cation polymerization catalyst may be conducted at a temperature of about 120~400° C. (particularly about 150~300° C., and more particularly about 180~250° C.). As such, the reaction may be implemented for about 1 min~24 hr, and particularly for about 30 min~5 hr. Alternatively, the oligomerization may be carried out in a continuous mode (e.g. using a CSTR reactor). As such, the space velocity (WHSV) may be set to about 0.01~10 hr$^{-1}$, and particularly about 0.1~5 hr$^{-1}$. Also, coke formed on the catalyst after oligomerization may be simply removed by air burning or firing, so that the activity of the catalyst may be close to the initial state.

Meanwhile, when the metallocene or Ziegler-Natta catalyst is used, the reaction may be carried out within a batch reactor at a temperature of about 100° C. or less, but the present invention is not necessarily limited thereto.

The olefinic lube base oil resulting from oligomerization may be adjusted so as to have the following properties.

Dimer (D) content: about 10~100 wt % (particularly about 50~80 wt %)

Trimer or higher (T+) content: about 1~100 wt % (particularly about 10~50 wt %)

Ratio of dimer/trimer or higher (D/T+ ratio; weight basis): about 0.1~100 (particularly, about 1~4)

Chain length (the number of carbon atoms of the longest carbon chain in the oligomer molecular structure): about 16~36

Hydrofinishing

In an embodiment of the present invention, the olefinic lube base oil produced by oligomerization contains a double bond in the molecular structure thereof. Thus, taking into consideration the oxidation stability of the final product, removal of the double bond is desirable. To this end, the double bond may be saturated and thus removed by hydrofinishing, which is known in the art.

One of the important properties of lube base oil is oxidation stability. The oxidation stability may refer to the extent of denaturalization based on bonding with oxygen in air. Since the bonding with oxygen may cause discoloration and corrosion, the lube base oil should not have any unsaturated double bond.

However, the olefinic lube base oil, which is produced by oligomerization of the olefin, essentially contains an unsaturated double bond. The unsaturated double bond in the olefin may be saturated by hydrogen ($H_2$) and may thus be removed, resulting in lube base oil.

Upon hydrofinishing, a catalyst used for hydrofinishing in a typical refining process may be used without particular limitation. Specifically, the metal therefor may include any one selected from among Groups 8, 9, 10, 11 and 12 metals on the periodic table, and may particularly include at least one selected from among platinum (Pt), palladium (Pd), nickel (Ni), iron (Fe), copper (Cu), chromium (Cr), vanadium (V), and cobalt (Co). More particularly useful are platinum (Pt) and/or palladium (Pd).

Also, the above metal may be loaded on an inorganic oxide support, and particularly at least one support selected from among alumina, silica, silica-alumina, zirconia, ceria, titania, zeolite (e.g. Y zeolite (having an SAR of about 12 or more)), clay, SAPO, and AlPO.

The reaction conditions for hydrofinishing may include a reaction temperature of about 150~500° C. (particularly about 180~350° C., and more particularly about 200~350° C.), a hydrogen ($H_2$) pressure of about 5~200 bar (particularly about 20~180 bar), and a GOR ($H_2$/feed ratio) of about 300~2000 Nm$^3$/m$^3$ (particularly about 500~1500 Nm$^3$/m$^3$).

In a continuous mode (e.g. using a CSTR reactor), the space velocity (WHSV) may be set to about 0.1~5 hr$^{-1}$, particularly about 0.1~3 hr$^{-1}$, and more particularly about 0.1~1 hr$^{-1}$.

As mentioned above, C16 and C18 linear internal olefins resulting from dehydration following hydrogenation of the biomass-derived fatty acid have a pour point of less than −9° C., and may satisfy the requirements of drilling fluids, and may thus be utilized as a high-quality drilling fluid. Also, the drilling fluid may be a linear or branched hydrocarbon containing an olefin, without aromatics.

Also, the lube base oil obtained by subjecting the biomass-derived fatty acid to hydrogenation, dehydration, oligomerization and hydrofinishing may be branched paraffin having 32 or more carbon atoms, and is a hydrocarbon material having an X-shaped structure, and thus may exhibit a viscosity index of at least 137, a pour point of about −24° C. or less, and a cloud point of −20° C. or less. As mentioned above, even when no additional isomerization is conducted, the resulting lube base oil satisfies the pour point and cloud point requirements, advantageously avoiding additional process costs.

When specific lube base oil having superior low-temperature properties is manufactured, depending on the end use, isomerization may be optionally performed. The isomerization process may be conducted in the presence of a catalyst configured such that a Group 10 metal (e.g. a precious metal such as Pt or Pd) alone or a combination thereof is supported on mesoporous zeolite (EU-1, ZSM-35, ZSM-11, ZSM-57, NU-87, ZSM-22, EU-2, EU-11, ZBM-30, ZSM-48, ZSM-23 or combinations thereof).

A better understanding of the present invention may be obtained via the following examples which are set forth to illustrate, but are not to be construed as limiting the present invention.

Example 1

Conversion of C18 Fatty Acid into C18 Alcohol Using CuCr/Al$_2$O$_3$ Catalyst

C18 stearic acid was converted into stearyl alcohol using a fixed-bed reactor containing a CuCr/Al$_2$O$_3$ catalyst. Specifically, 6 g of a commercially available CuCr/Al$_2$O$_3$ catalyst was placed in a fixed-bed reactor, the top and bottom of the catalyst were closed with glass wool, the remaining portion of the reactor was filled with silica beads, and a thermocouple was disposed so as to be in contact with the catalyst. The reaction temperature was increased to about 400° C. under conditions of about N$_2$ 200 sccm and H$_2$ 200 sccm, and the reactor was heated at a rate of about 5° C./min, and then maintained for 3 hr at a reaction pressure of about 50 bar. Thereafter, the reaction temperature was decreased to about 300° C., and then a mixed solution of C18 fatty acid and ethanol at a molar ratio of 1:5 was fed at about 0.13 sccm, and the reactor was operated at a space velocity (WHSV) of about 1 hr$^{-1}$. Draining for the first 16 hr and then sampling at 8-hr intervals were performed, and hydrogenation activity and selectivity were measured. The reaction activity was measured at about 300° C., after which changes in the reaction activity were checked depending on changes in the reaction temperature and pressure. Taking into consideration the reaction stability, the stabilized product pattern results two days after changes in the reaction conditions were adopted. The conversion rate of the product was measured via SimDist analysis. The product selectivity and the presence or absence of side reactions were measured via GC-MS and SimDist analysis. The results are shown in Table 6 below.

TABLE 6

|  |  | CuCr/Al$_2$O$_3$ | | | |
| --- | --- | --- | --- | --- | --- |
| Sample ID |  | 47 | 39 | 28 | 58 |
| Reaction conditions | Temp. (° C.) | 320 | 320 | 360 | 320 |
|  | H$_2$ pressure (bar) | 50 | 40 | 40 | 40 |
|  | H$_2$ flow rate (sccm) | 200 | 200 | 200 | 100 |
| Product pattern (%) | C17, C18 Paraffin | 0 | 0 | 0 | 0 |
|  | C18 Alcohol | 83 | 79 | 46 | 67 |
|  | C18 Acid | 4 | 13 | 21 | 11 |
|  | C18 α-olefin | 0 | 0 | 0 | 4 |
|  | C18 Acid-ethyl ester | 13 | 8 | 7 | 19 |
|  | Others | 0 | 0 | 25 | 0 |

Figure 3:
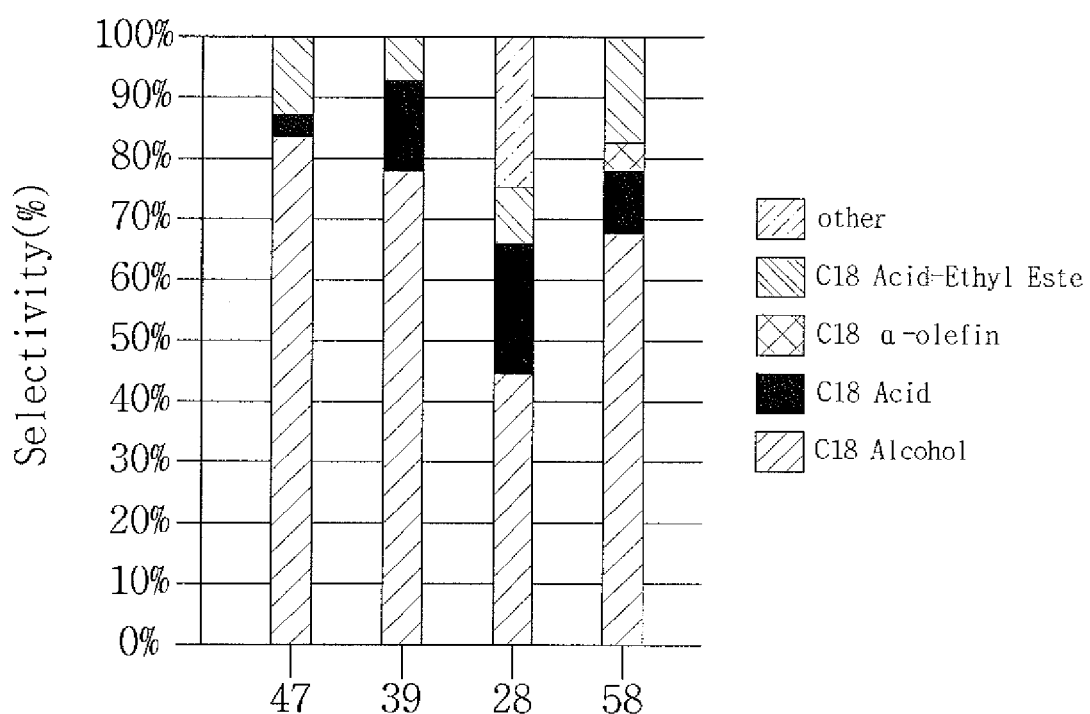
FIG. 3 is a graph illustrating the selectivity of C18 fatty acid resulting from hydrogenation of C18 stearic acid using a $CuCr/Al_2O_3$ catalyst in Example 1 according to the present invention.

As is apparent from Table 6 and FIG. 3, the CuCr/Al$_2$O$_3$ catalyst exhibited a high conversion rate of C18 fatty acid and high selectivity of C18 alcohol. The yield of C18 alcohol was 80% or more under conditions of a reaction temperature of about 320° C., an H$_2$ pressure of 50 bar, and an H$_2$ flow rate of 200 sccm. As such, side reactions did not occur. However, as the reaction temperature was increased (to 360° C. or higher), side reactions such as the formation of heavy hydrocarbons occurred, and the conversion rate was somewhat decreased. Furthermore, when the H$_2$ flow rate was lowered and thus the catalyst retention time of the reaction feed was increased, a small amount of C18 linear alpha olefin was produced. However, this amount was very low, about 4%, thus making it possible to industrially apply the above product.

Example 2

Conversion of C18 Fatty Acid into C18 Alcohol Using Cu/SiO$_2$ Catalyst

C18 stearic acid was converted into stearyl alcohol using a fixed-bed reactor containing a Cu/SiO$_2$ catalyst. This reaction was carried out under the same operating conditions as in Example 1, with the exception that a commercially available Cu/SiO$_2$ catalyst was used. The Cu/SiO$_2$ catalyst was composed of 76% CuO and 14% SiO$_2$, with MgO (3 wt %), Cr$_2$O$_3$ (1.5 wt %), and graphite (2 wt %). Likewise, the product was measured for the reaction conversion rate, selectivity and the presence or absence of side reactions through SimDist and GC-MS analysis. The results are shown in Table 7 below.

TABLE 7

|  |  | Cu/SiO$_2$ | | | |
| --- | --- | --- | --- | --- | --- |
| Sample ID |  | 19 | 24 | 34 | 53 |
| Reaction conditions | Temp. (° C.) | 300 | 350 | 400 | 320 |
|  | H$_2$ pressure (bar) | 40 | 40 | 40 | 40 |
|  | H$_2$ flow rate (sccm) | 200 | 200 | 200 | 100 |
| Product pattern (%) | C17, C18 Paraffin | 22 | 32 | 33 | 0 |
|  | C18 Alcohol | 54 | 45 | 40 | 67 |
|  | C18 Acid | 0 | 0 | 0 | 11 |
|  | C18 α-olefin | 0 | 0 | 0 | 4 |
|  | C18 Acid-ethyl ester | 15 | 17 | 17 | 19 |
|  | Others | 9 | 6 | 10 | 0 |

Figure 4:
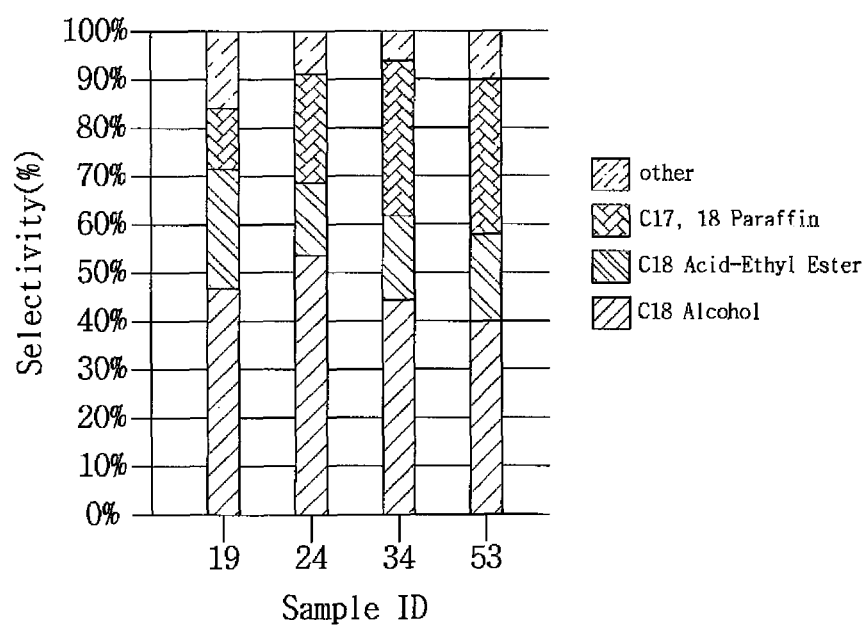
FIG. 4 is a graph illustrating the selectivity of C18 alcohol resulting from hydrogenation of C18 stearic acid using a $Cu/SiO_2$ catalyst in Example 2 according to the present invention.

As is apparent from Table 7 and FIG. 4, the Cu/SiO$_2$ catalyst exhibited the C18 alcohol selectivity of about 54%, which was lower than the yield of Example 1 using the CuCr/Al$_2$O$_3$ catalyst. Also, side reactions took place at a low temperature of 300° C., including the production of heavy hydrocarbons having a boiling point of 480° C. or higher and the formation of C17 and C18 paraffin. Furthermore, as the reaction temperature was higher, the selectivity of C17 and C18 paraffin was drastically increased, and the selectivity of the target product C18 alcohol was gradually decreased. However, the yield of C18 alcohol was 40~54%, and thus this catalyst manifested usability as a candidate catalyst for the production of C18 alcohol.

Example 3

Figure 5:
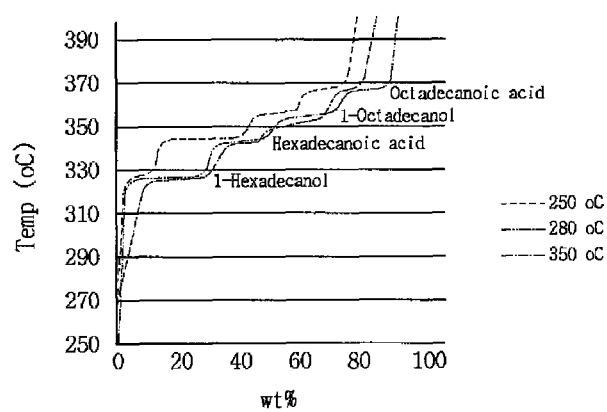
FIG. 5 is a graph illustrating the reaction conversion rates, based on SimDist and GC-MS analysis, of products resulting from hydrogenation of a palm fatty acid distillate using a $CuZnAlO_x$ catalyst in Example 3 according to the present invention.
Figure 6:
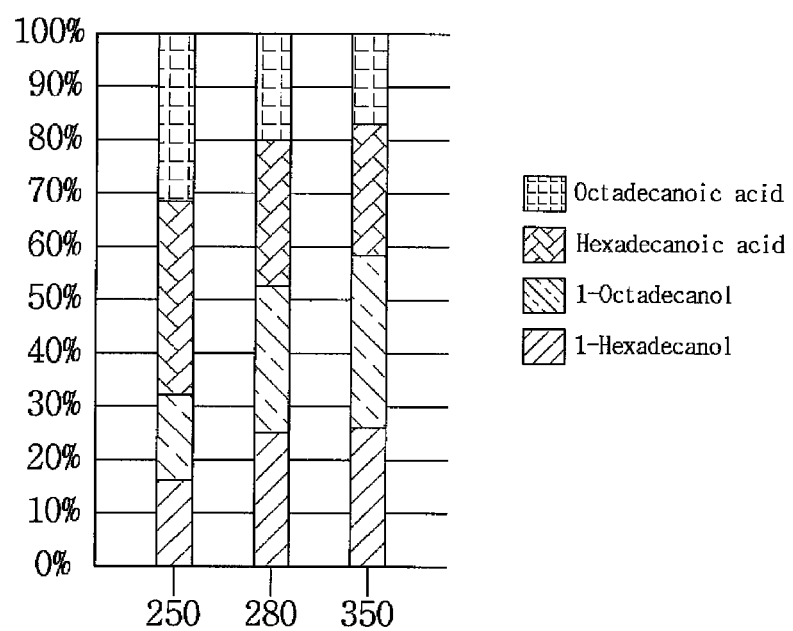
FIG. 6 is a graph illustrating the yields, based on SimDist and GC-MS analysis, of products resulting from the hydrogenation of a palm fatty acid distillate using a $CuZnAlO_x$ catalyst in Example 3 according to the present invention.

Conversion of Palm Fatty Acid Distillate (PFAD) into C16 and C18 Fatty Alcohol Using CuZnCrO$_x$ Catalyst This reaction was carried out under the same operating conditions as in Example 1, with the exception that a palm fatty acid distillate was used as the feed, instead of the C18 fatty acid, and a commercially available CuZnCrO$_x$ catalyst was used. The CuZnCrO$_x$ catalyst used had a specific surface area of about 78 m$^2$/g, a total pore volume of 3.5 cc/g, and CuO/ZnO/Cr$_2$O$_3$=15~20/25~35/35~50 wt %. Likewise, the product was measured for the reaction conversion rate, the selectivity and the presence or absence of side reactions through SimDist and GC-MS analysis. The results are graphed in FIGS. 5 and 6.

The palm fatty acid distillate feed seldom caused side reactions in the presence of the CuZnCrOx catalyst. The yield indicates the yield of C16 and C18 fatty alcohol of about 58% at a reaction temperature of about 350° C. This low yield may be increased thorough recycling because side reactions do not occur, and thus the palm fatty acid distillate is sufficiently industrially applicable.

Example 4

Evaluation of Dehydration Activity of C16 and C18 Fatty Alcohol

The C16 and C18 fatty alcohols obtained in Example 3 were evaluated for dehydration activity in the presence of an alumina catalyst using a fixed-bed reactor. Specifically, 6 g of an alumina catalyst was placed in a fixed-bed reactor, the top and bottom of the catalyst were closed with glass wool, the remaining portion of the reactor was filled with silica beads, and a thermocouple was disposed so as to be in contact with the catalyst. The alumina had a surface area of about 260 m$^2$/g, an average pore size of about 10 nm, and a total pore volume of about 0.83 cc/g. The reactor was heated at a rate of 5° C./min under conditions of about N$_2$ 5 bar and 100 sccm, and maintained at about 500° C. for 3 hr, so that water was removed from the surface of the catalyst or the adsorbed gas was removed. Thereafter, the temperature was lowered to about 300° C., and a mixture of C16 and C18 fatty alcohols and n-heptane at a molar ratio of 6:4 was fed at 0.13 sccm and the reactor was operated at a space velocity (WHSV) of about 1 hr$^{-1}$. Draining for the first 16 hr and then sampling at 8-hr intervals were performed, and the conversion activity of linear internal olefins and the selectivity thereof were measured. The reaction activity was measured at 300° C., after which the reaction temperature was increased to 500° C. in 50° C. increments, and the reaction activity was also measured. Taking into consideration the reaction stability, the stabilized product pattern results two days after changes in the reaction conditions were adopted. The conversion rate of the produced linear internal olefin was measured through SimDist analysis. The produced gas was analyzed through GC, and the selectivity of the product and the presence or absence of side reactions were measured through GC-MS and SimDist analysis. Also, in order to check the applicability of the produced linear internal olefin as a drilling fluid, the pour point and the cloud point were analyzed.

Figure 7:
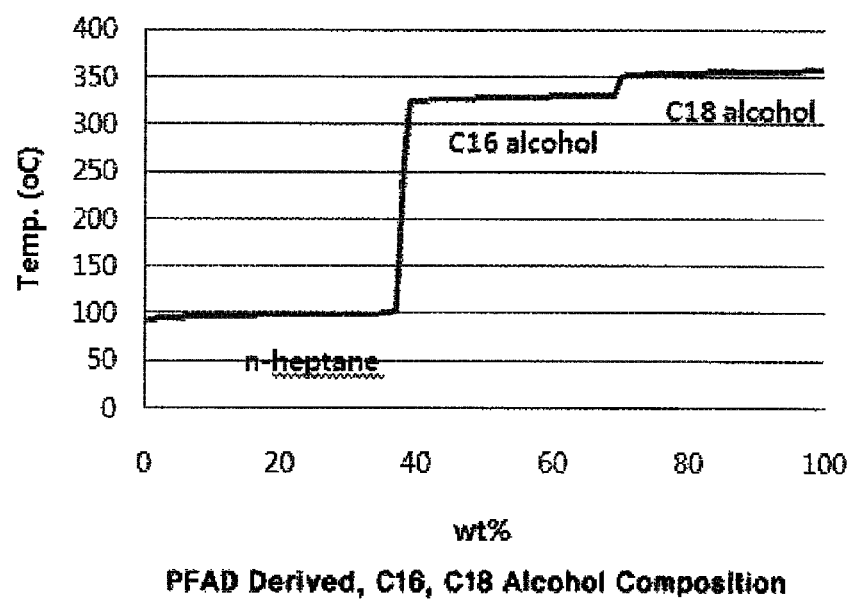
FIG. 7 is a graph illustrating the results of SimDist analysis of C16 and C18 fatty alcohols derived from a palm fatty acid distillate in Example 4 according to the present invention.

FIG. 7 is a graph illustrating the results of SimDist analysis of C16 and C18 fatty alcohols derived from the palm fatty acid distillate feed. As shown in the SimDist pattern, the fatty alcohol derived from the palm fatty acid distillate was composed of C16 and C18 alcohols at a ratio of about 1:1 (51.3:48.7 wt %).

Figure 8:
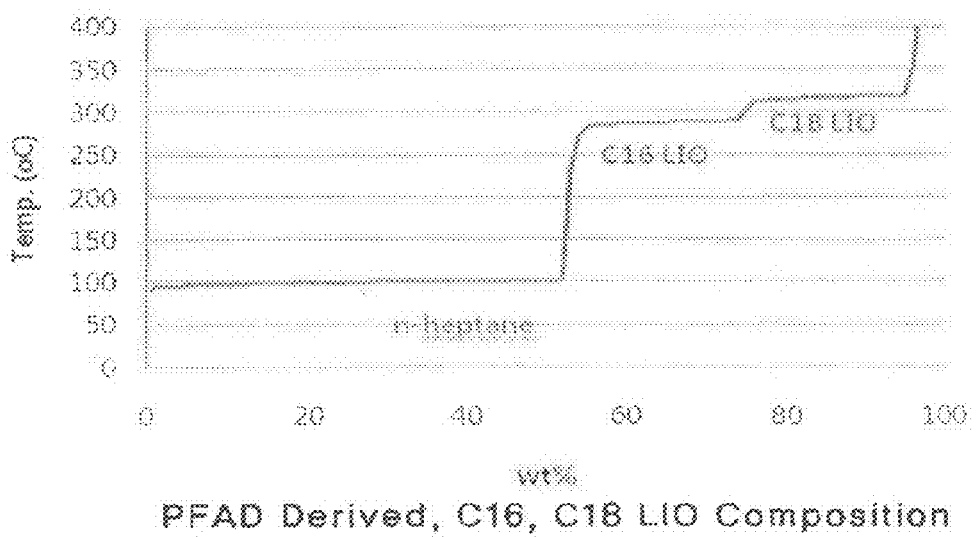
FIG. 8 is a graph illustrating the SimDist pattern of products via dehydration in Example 4 according to the present invention.

The product obtained by dehydrating the feed having the above composition under the above testing conditions was subjected to SimDist analysis. The resultant SimDist pattern is shown in FIG. 8.

Figure 11:
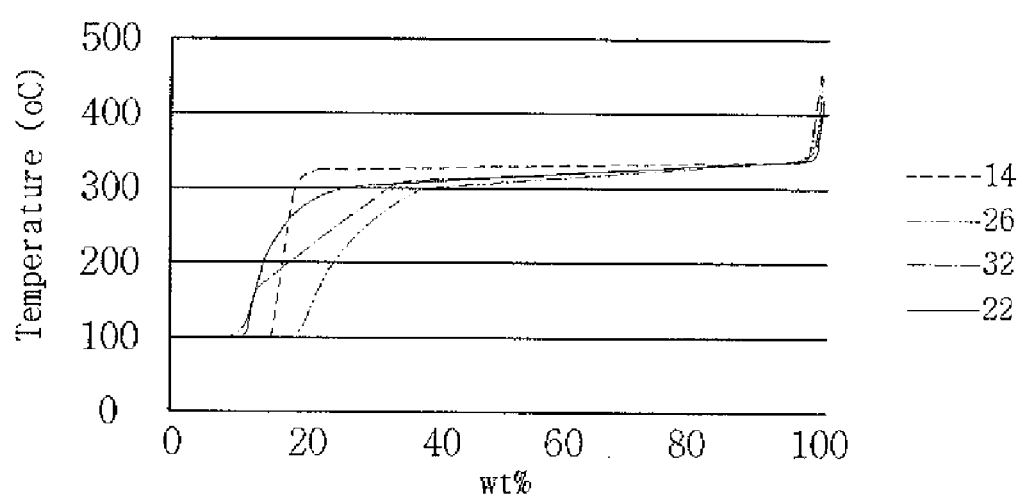
FIG. 11 is a graph illustrating the SimDist pattern, depending on changes in the reaction temperature, of the products resulting from the dehydration of C16 and C18 fatty alcohols in Example 4 according to the present invention.

As shown in FIG. 11, based on the dehydration results, it was possible to convert the C16 and C18 fatty alcohols into C16 and C18 linear internal olefins at a high conversion rate of 95% or more. The remainder of less than 5% was determined to be an ester intermediate. Based on the evaluation results of dehydration activity, the selectivity and yield of the C16 and C18 linear internal olefins as the target product were very high, and there were no side reactions, thus achieving high industrial applicability thereof.

Figure 9:
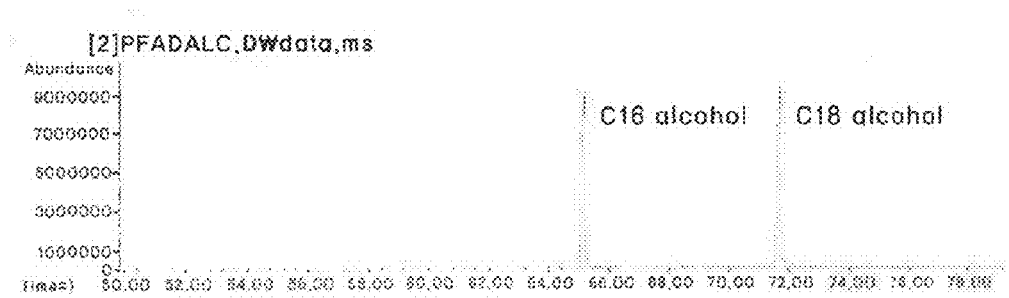
FIG. 9 is a graph illustrating the results of GC-MS analysis of C16 and C18 fatty alcohol mixtures before the dehydration in Example 4 according to the present invention.

The materials before and after dehydration were subjected to GC-MS analysis. The results are shown in FIG. 9. FIG. 9 illustrates the results of GC-MS analysis of the C16 and C18 fatty alcohol mixture used as the dehydration feed. As shown in FIG. 9, the C16 and C18 alcohols were present alone.

Figure 10:
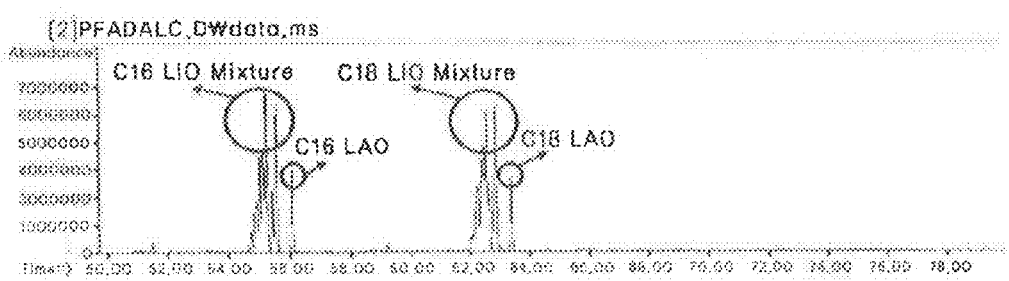
FIG. 10 is a graph illustrating the results of GC-MS analysis of C16 and C18 linear alpha olefin (LAO) mixtures and linear internal olefin (LIO) mixtures among the products after the dehydration in Example 4 according to the present invention.

The product obtained by dehydrating the feed having the above composition was subjected to GC-MS analysis. The results are shown in FIG. 10.

The linear olefin obtained by dehydration was composed of linear alpha olefin and linear internal olefin mixed together, and there was no cracking byproduct. Based on the analytical results of FIG. 10, the product obtained by dehydration was mainly an internal olefin mixture, rather than the alpha olefin mixture. The produced linear olefin mixture was analyzed to determine the pour point and cloud point. The results are given in Table 8 below.

TABLE 8

| Dehydration Temp. (° C.) | Pour point (° C.) | Cloud point (° C.) |
| --- | --- | --- |
| 400 | −9 | −10 |

C16 and C18 linear alpha olefins derived from full-range linear alpha olefins have pour points of 2° C. and 18° C., respectively. Since a drilling fluid has to possess a pour point of less than −5° C., the C16 and C18 linear alpha olefins derived from full-range linear alpha olefins cannot be directly utilized as a drilling fluid. Currently, a mixture of C14 and C16 linear alpha olefins derived from full-range linear alpha olefins may be employed as a drilling fluid product.

However, as shown in Table 8, when such olefins were converted into linear internal olefins, it was possible to lower the pour point to less than −9° C. Furthermore, such olefins are a biomass fat-derived drilling fluid, and the value thereof is thus regarded as large.

TABLE 9

| | Cu/SiO$_2$ | | | |
| --- | --- | --- | --- | --- |
| Sample ID | 14 | 26 | 32 | 22 |
| Reaction conditions Temp. (° C.) | 400 | 500 | 500 | 500 |
| Feed rate (sccm) | 0.13 | 0.13 | 0.07 | 0.13 |
| N$_2$ flow rate (sccm) | 50 | 50 | 50 | 200 |
| Reaction feature | | Cracking and isomerization occur | | |

As is apparent from Table 9 and FIG. 11, side reactions such as cracking and skeletal isomerization did not occur at 400° C., but cracking and skeletal isomerization occurred when the reaction temperature was increased to 500° C.

Consequently, when the palm fatty acid distillate was used as the feed, it could be converted into C16 and C18 linear internal olefin mixtures and linear alpha olefin mixtures without side reactions. Taking into consideration the recycling, the feed could be completely converted into the linear internal olefin mixtures and linear alpha olefin mixtures without loss. The resulting C16 and C18 linear internal olefin mixtures and linear alpha olefin mixtures contained no aromatics and had a pour point of about −9° C. and thus were found to be applicable as a drilling fluid. Furthermore, when the reaction conditions were additionally changed, the position shift reaction of the double bond in the olefin was activated, remarkably lowering the pour point.

Example 5

Conversion of C16 and C18 Linear Alpha Olefin Mixtures and Linear Internal Olefin Mixtures into Lube Base Oil About 200 of the C16 and C18 linear alpha olefin mixtures and linear internal olefin mixtures of Example 4 and also 20 g of an oligomerization catalyst zeolite were placed in a 500 cc glass flask. Then, the reaction mixture was heated to 180° C. with stirring at about 500 rpm. When the reaction temperature reached 180° C. the reaction was maintained for about 3 hr and then stopped. As the zeolite catalyst, Y-zeolite, specifically Y-zeolite having an SAR of 80 was used. After termination of the reaction, the mixture of the catalyst and the reaction product was filtered, thus separating the catalyst and the reaction product from each other. The catalyst was stored for recycling, and the reaction product was stored for subsequent hydrofinishing. The hydrofinishing reaction was carried out using a NiMo/ZrO$_2$ catalyst in a CSTR reactor. As such, the reaction conditions included a temperature of about 200° C., an H$_2$ pressure of 20 bar, a space velocity (WHSV) of 0.5 hr$^{-1}$ and GOR of 1000 Nm$^3$/m$^3$, thereby selectively removing the double bond from the reaction product. The final reaction product was measured for the reaction yield through SimDist analysis, and for the presence or absence of side reactions through GC-MS analysis. In order for the reaction product to possess properties suitable for use as lube base oil, the viscosity was measured at about 40° C. and 100° C., on the basis of which the viscosity index was calculated. Furthermore, the pour point of the oligomer of C18 linear internal olefin was measured, whereby the applicability thereof as lube base oil was checked. The test results are shown in the following table and the appended graph.

TABLE 10

| Oligomerization Temp. (° C.) | PP/CP of Olefin (° C./° C.) | Yield of converted lube base oil (%) | Viscosity (cps) 40° C. | Viscosity (cps) 100° C. | Viscosity index (a.u.) | Pour point (° C.) |
|---|---|---|---|---|---|---|
| 250 | −9/10 | 50 | 24.08 | 4.99 | 137 | −24 |

Figure 12:
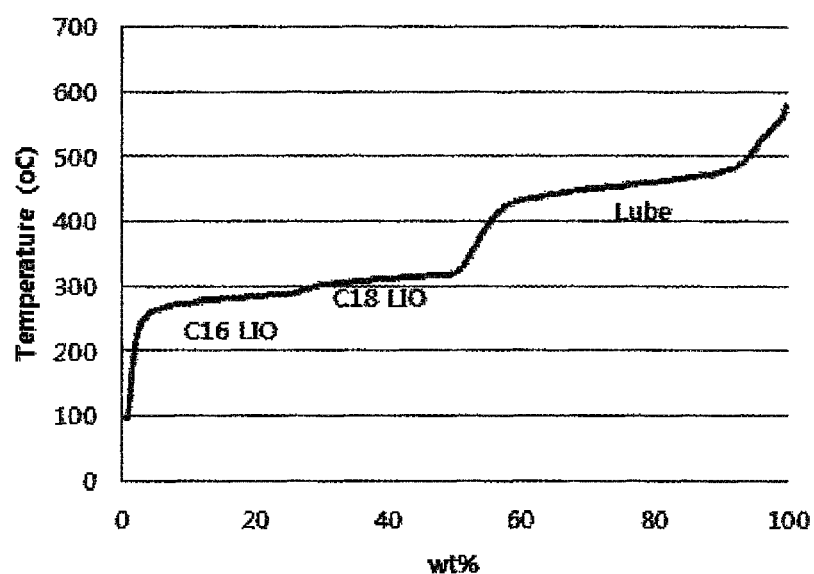
FIG. 12 is a graph illustrating the SimDist pattern of the product resulting from the oligomerization and hydrofinishing of C16 and C18 linear alpha olefin mixtures and linear internal olefin mixtures in Example 5 according to the present invention.

As is apparent from Table 10 and FIG. 12, the yield of lube base oil converted by oligomerization was about 50%, but could be additionally increased, in consideration of the recycling, due to the absence of other side reactions. As illustrated in FIG. 12, the reason why there is a slope in the lube base oil zone in the SimDist pattern is that the linear alpha olefin and the linear internal olefin for lube base oil are composed of C16 and C18 linear alpha olefin mixtures and linear internal olefin mixtures, rather than individual materials in isolation.

Accordingly, simple modifications or variations of the present invention fall within the scope of the present invention as defined in the accompanying claims.

What is claimed is:

1. A method of preparing a drilling fluid and lube base oil using a fatty acid derived from a biomass, comprising:
   a) providing a biomass-derived fatty acid mixture, the biomass-derived fatty acid mixture containing at least 80 wt % of C16 fatty acid and C18 fatty acid, wherein a C16 fatty acid weight to C18 fatty acid weight ratio is 0.25 to 1;
   b) hydrogenating the biomass-derived fatty acid mixture to give a fatty alcohol mixture;
   c) dehydrating the fatty alcohol mixture to convert the fatty alcohol mixture into a C16 and C18 linear internal olefin mixture at a conversion rate of 95 wt % or more;
   d) oligomerizing the C16 and C18 linear internal olefin mixture to give olefinic lube base oil; and
   e) hydrofinishing the olefinic lube base oil, yielding Group III lube base oil,
   wherein the C16 and C18 linear internal olefin mixture in c) is an olefinic hydrocarbon-based drilling fluid,
   wherein the dehydrating in c) is performed under conditions of a temperature 400-500° C. and a space velocity of 0.01-50 hr$^{-1}$.

2. The method of claim 1, wherein the biomass is animal biomass, plant biomass, or a combination thereof,
   the animal biomass comprises fish oil, cattle oil, lard, sheep oil, or butter, and
   the plant biomass comprises sunflower seed oil, canola oil, coconut oil, corn oil, cottonseed oil, rapeseed oil, linseed oil, safflower oil, oat oil, olive oil, palm oil, peanut oil, apricot kernel oil, almond oil, avocado oil, camellia oil, rice bran oil, walnut oil, rape oil, flaxseed oil, sesame oil, soybean oil, castor oil, cocoa butter, or palm kernel oil.

3. The method of claim 1, wherein the biomass-derived fatty acid mixture provided in a) has 4 to 24 carbon atoms.

4. The method of claim 1, wherein the biomass-derived fatty acid mixture provided in a) is a fatty acid mixture produced by de-esterification of a triglyceride in the biomass.

5. The method of claim 1, wherein the biomass-derived fatty acid mixture is a palm fatty acid distillate (PFAD) separated from the biomass.

6. The method of claim 1, wherein the hydrogenating in b) is performed in the presence of a metal-carrier catalyst, and the metal-carrier catalyst comprises at least one metal selected from Groups 8 to 11 metals on a periodic table is loaded on at least one carrier selected from alumina ($Al_2O_3$), silica ($SiO_2$), silica-alumina, zeolite, mesoporous silica, SAPO, and AlPO.

7. The method of claim 6, wherein the metal comprises at least one selected from copper (Cu), chromium (Cr), zinc (Zn), and aluminum (Al).

8. The method of claim 1, wherein the hydrogenating in b) is performed under conditions of a temperature of 150-500° C. and a pressure of 100 bar or less.

9. The method of claim 1, wherein the hydrogenating in b) is performed under conditions of a temperature of 250-400° C. and a pressure of 50 bar or less.

10. The method of claim 1, wherein the dehydrating in c) is performed in the presence of a metal oxide catalyst, and the metal oxide catalyst comprises alumina, silica-alumina, kaolin clay, SAPO, AlPO, zirconia, titania, iron oxide, vanadium oxide, zeolite, alumina-loaded mesoporous silica, or mixtures thereof.

11. The method of claim 1, wherein the oligomerizing in d) is performed in the presence of a cation polymerization catalyst.

12. The method of claim 11, wherein the cation polymerization catalyst comprises at least one selected from the group of aluminum (Al) loaded on zeolite, clay, SAPO, AlPO, or mesoporous silica.

13. The method of claim 1, wherein the oligomerizing in d) is performed at 120-400° C.

14. The method of claim 1, wherein the hydrofinishing in e) is performed using a catalyst comprising at least one metal selected from platinum (Pt), palladium (Pd), nickel (Ni), iron (Fe), copper (Cu), chromium (Cr), vanadium (V), and cobalt (Co) loaded on at least one support selected from alumina, silica, silica-alumina, zirconia, ceria, titania, zeolite, clay, SAPO, and AlPO.

15. The method of claim 1, wherein the hydrofinishing in e) is performed under conditions of a temperature of 150-500° C., and $H_2$ pressure of 5-200 bar, and a gas oil ratio ($H_2$/feed oil ratio) of 300-2000 Nm$^3$/m$^3$.

16. The method of claim 1, wherein the drilling fluid is a linear or branched hydrocarbon having a pour point of −9° C. or less and containing an olefin, without aromatics.

17. The method of claim 1, wherein the lube base oil is branched paraffin having 32 or more carbon atoms.

18. The method of claim 1, wherein the lube base oil has a viscosity index of at least 137, a pour point of −24° C. or less, and a cloud point of −20° C. or less.

19. The method of claim 1, wherein the oligomerizing in d) is performed in the presence of a metallocene catalyst or a Ziegler-Natta catalyst.

20. The method of claim 19, wherein the oligomerizing in d) is performed within a batch reactor at a temperature of 100° C. or less.

* * * * *

UNITED STATES PATENT AND TRADEMARK OFFICE
CERTIFICATE OF CORRECTION

| | |
|---|---|
| PATENT NO. | : 9,909,047 B2 |
| APPLICATION NO. | : 14/728258 |
| DATED | : March 6, 2018 |
| INVENTOR(S) | : Hee Jung Jeon et al. |

It is certified that error appears in the above-identified patent and that said Letters Patent is hereby corrected as shown below:

On the Title Page

Under (71) Applicant:
Please replace the second applicant name from "SK LUBRICANTS CO., LTD., Seoul (KR)" to "SK ENMOVE CO., LTD., Seoul (KR)"; and Under (73) Assignee:
Please replace the second assignee name from "SK LUBRICANTS CO., LTD., Seoul (KR)" to "SK ENMOVE CO., LTD., Seoul (KR)".

Signed and Sealed this
Thirteenth Day of August, 2024

Katherine Kelly Vidal
*Director of the United States Patent and Trademark Office*